United States Patent
Elder et al.

(10) Patent No.: US 9,291,593 B2
(45) Date of Patent: Mar. 22, 2016

(54) DUAL-CHAMBER ANALYTICAL TEST STRIP

(71) Applicant: Cilag GmbH International, Zug (CH)

(72) Inventors: David Elder, Inverness (GB); Steven Setford, Inverness (GB); Allan Faulkner, Inverness (GB); Ryan Walsh, Inverness (GB)

(73) Assignee: Cilag GmbH International, Zug (CH)

( * ) Notice: Subject to any disclaimer, the term of this patent is extended or adjusted under 35 U.S.C. 154(b) by 88 days.

(21) Appl. No.: 14/087,453

(22) Filed: Nov. 22, 2013

(65) Prior Publication Data

US 2015/0144505 A1  May 28, 2015

(51) Int. Cl.
*G01N 27/327* (2006.01)
*A61B 5/05* (2006.01)
*C12Q 1/00* (2006.01)

(52) U.S. Cl.
CPC .............. *G01N 27/3272* (2013.01); *A61B 5/05* (2013.01); *C12Q 1/006* (2013.01); *G01N 27/3273* (2013.01)

(58) Field of Classification Search
None
See application file for complete search history.

(56) References Cited

U.S. PATENT DOCUMENTS

| | | |
|---|---|---|
| 6,193,873 B1 | 2/2001 | Ohara et al. |
| 6,444,115 B1 | 9/2002 | Hodges et al. |
| 6,663,833 B1 | 12/2003 | Stave et al. |
| 6,676,995 B2 | 1/2004 | Dick et al. |
| 6,689,411 B2 | 2/2004 | Dick et al. |
| 6,749,887 B1 | 6/2004 | Dick et al. |
| 6,830,934 B1 | 12/2004 | Harding et al. |
| 7,144,485 B2 | 12/2006 | Hsu et al. |
| 7,199,594 B2 | 4/2007 | Kermani |
| 7,291,256 B2 | 11/2007 | Teodorczyk et al. |
| 7,674,616 B2 | 3/2010 | Farnam, III et al. |
| 7,955,484 B2 | 6/2011 | Cai et al. |
| 8,163,162 B2 | 4/2012 | Chatelier et al. |
| 2004/0120848 A1 | 6/2004 | Teodorczyk |
| 2007/0074977 A1 | 4/2007 | Guo et al. |
| 2007/0084734 A1 | 4/2007 | Roberts et al. |
| 2007/0087397 A1 | 4/2007 | Kraft et al. |
| 2007/0131549 A1* | 6/2007 | Cai et al. ............... 204/403.02 |
| 2007/0287191 A1* | 12/2007 | Stiene et al. ................ 436/150 |
| 2011/0094896 A1* | 4/2011 | MacFie et al. ............. 205/777.5 |
| 2011/0139634 A1 | 6/2011 | Chou et al. |
| 2012/0193228 A1* | 8/2012 | Hsu ......................... 204/403.01 |

FOREIGN PATENT DOCUMENTS

| | | |
|---|---|---|
| WO | WO 97/18465 A1 | 5/1997 |
| WO | 2004062494 A1 | 7/2004 |
| WO | WO 2010/049669 A1 | 5/2010 |

OTHER PUBLICATIONS

International Search Report and Written Opinion issued in related International Patent Application No. PCT/EP2014/075239, dated Mar. 12, 2015, 12 pages.

* cited by examiner

*Primary Examiner* — Jennifer Dieterle

(57) ABSTRACT

An analytical test strip can include a patterned definition layer defining two fluidically-separated sample cells having respective ports, a common electrode arranged over the definition layer and in electrical communication with each of the cells, and respective cell electrodes. Surface portions of each electrode can be exposed. A method for testing a fluid sample using such a strip includes receiving a first fluid sample in the first sample cell and detecting a first electrical property thereof. It is then determined whether a second fluid sample should be added to the other sample cell. An analyte measurement system can include such a strip and test meter to receive the strip. The test meter can detect respective electrical properties of fluid samples in the cells.

20 Claims, 4 Drawing Sheets ically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

DUAL-CHAMBER ANALYTICAL TEST STRIP

TECHNICAL FIELD

The present invention generally relates to the field of analyte measurement, and more specifically to analytical test strips having at least two separate sample chambers as well as uses for such strips.

DESCRIPTION OF RELATED ART

The determination (e.g., detection or concentration measurement) of an analyte in a fluid sample is of particular interest in the medical field. For example, it can be desirable to determine glucose, ketone bodies, cholesterol, lipoproteins, triglycerides, acetaminophen or HbA1c concentrations in a sample of a bodily fluid such as urine, blood, plasma or interstitial fluid. Such determinations can be achieved using a test meter, e.g., a portable or hand-held test meter, in combination with analytical test strips (e.g., electrochemical-based analytical test strips). Analytical test strips generally include a sample cell (also referred to herein as a "reaction chamber," an "analyte chamber," or a "sample chamber") for maintaining a liquid analyte, e.g., whole blood, in contact with two or more electrodes. Analytes can then be determined electrochemically using signals conveyed by the electrodes.

Since test meters are used to make care decisions relating to medical conditions, it is desirable that these devices measure with as much accuracy and precision as possible. However, test meters are often employed by patients or other personnel that have not received formal medical training. Accordingly, there is an opportunity for user error in the introduction of a fluid sample into a sample cell. It is desirable to reduce or recover from user error. Moreover, biological measurements can be subject to various types of noise. It is sometimes desirable to measure multiple fluid samples of the same kind (e.g., multiple blood samples) to provide more accurate results, or to verify that a result was not corrupted by noise.

BRIEF DESCRIPTION OF THE DRAWINGS

Various novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
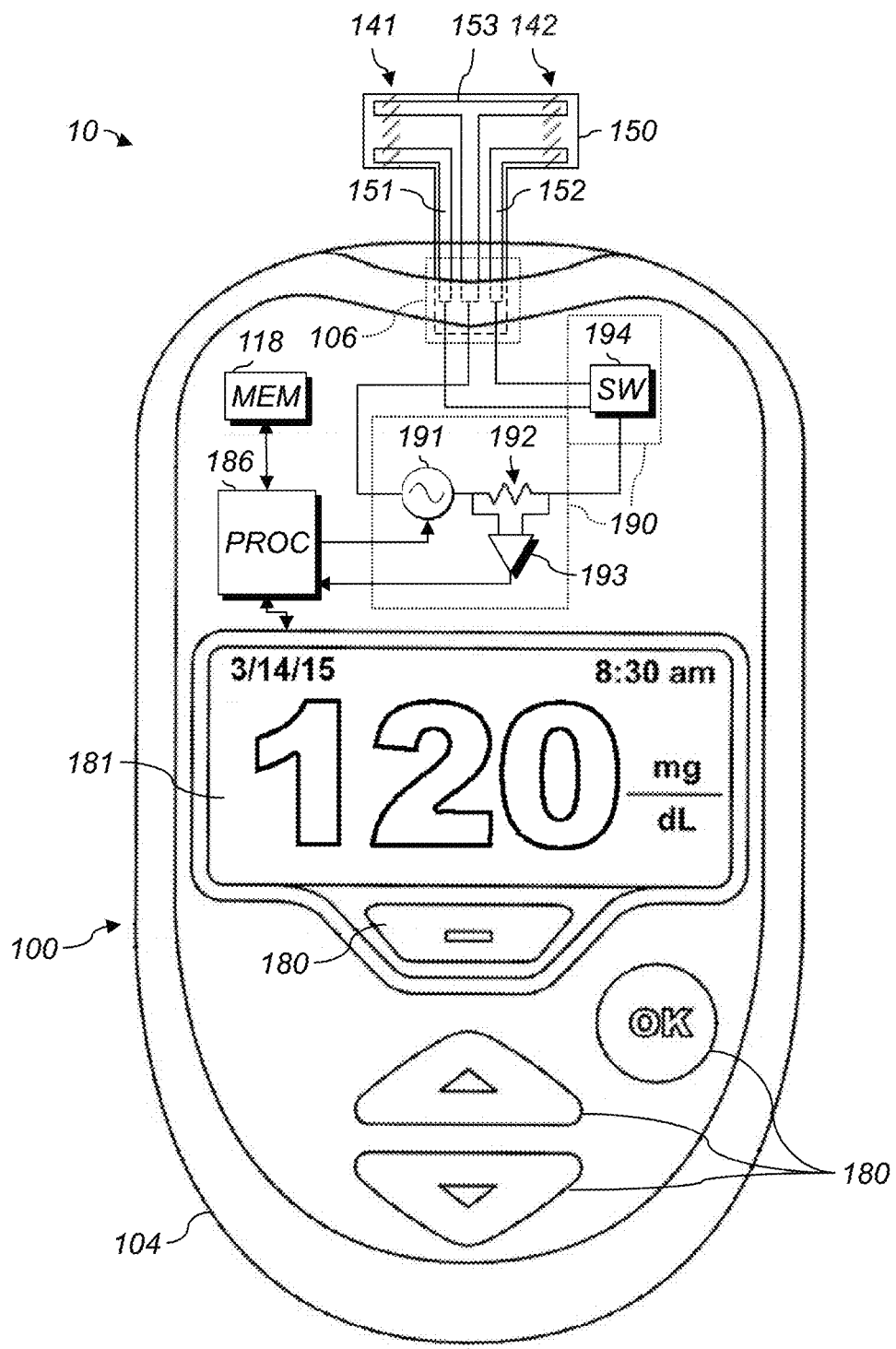
FIG. 1 is a simplified depiction of an exemplary analyte measurement system according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Throughout this description, some embodiments are described in terms that would ordinarily be implemented as software programs. Those skilled in the art will readily recognize that the equivalent of such software can also be constructed in hardware (hard-wired or programmable), firmware, or micro-code. Given the systems and methods as described herein, software or firmware not specifically shown, suggested, or described herein that is useful for implementation of any embodiment is conventional and within the ordinary skill in such arts.

As used herein, the terms "about" or "approximately" for any numerical values or ranges indicate a suitable dimensional tolerance that allows the part or collection of components to function for its intended purpose as described herein. In addition, the term "in", as used throughout this description, does not necessarily require that one component or structure be completely contained within another, unless otherwise indicated.

In general, analyte measurement systems according to embodiments of the present invention include an analytical test strip having two fluidically separated sample cells, and a test meter which is suitably adapted to receive the analytical test strip. The test meter has a processor configured to selectively detect an electrical property of a fluid sample in either of the sample cells.

Test meters according to embodiments of the present invention are beneficial in that they provide improved convenience of retests. It can be appropriate or necessary to test a second fluid sample directly after testing a first fluid sample, e.g., if the first fluid sample does not sufficiently fill a sample chamber, or if a user desires to verify a result, e.g., an unexpectedly-high or -low blood glucose reading. Various embodiments permit redundantly determining electrical properties of fluid samples (e.g., two blood samples) as an integrity check. For example, after a heavy meal, two different blood glucose readings can be taken.

A problem solved by various embodiments is that test strips often have very small ports to which it can be difficult for a user to reliably apply fluid. As described herein, if fluid is not correctly applied to the first sample cell, e.g., if not enough fluid is applied to the first sample cell, a second measurement can readily be taken using the second sample cell. Another problem solved by various embodiments is that analyte levels in biological fluids fluctuate over time. The greater the time interval between two repeat analyte measurements (e.g., from blood samples), the more likely that the two readings will not agree due to metabolic changes in analyte and interferent levels. Using a test strip with two sample chambers permits taking two readings without incurring between them the time required to change test strips. The two successive readings can therefore more effectively indicate the value of the analyte of interest (e.g., blood glucose) at a given time. Moreover, taking two independent readings and comparing or combining the two readings can advantageously reduce the influence of measurement noise on the reading. Measurement noise can originate from, e.g., electrical noise in the measurement circuit or physical variations of the dimensions of the sample cells within the manufacturing tolerances of the analytical test strip.

The concepts discussed herein can readily be incorporated by one of sufficient skill into a test meter. One example of a test meter that can be suitably configured is the commercially available OneTouch® Ultra® 2 glucose meter from LifeScan Inc. (Milpitas, Calif.). Additional examples of test meters that can also be modified are described in U.S. Patent Application Publication Nos. 2007/0084734 (published on Apr. 19, 2007) and 2007/0087397 (published on Apr. 19, 2007) as well as International Publication Number WO2010/049669 (published on May 6, 2010), each of which is hereby incorporated by reference in its entirety.

FIG. 1 shows an exemplary analyte measurement system 10. The system 10 includes an analytical test strip 150 (or "test strip" herein) comprising a patterned layer (not shown) defining two fluidically separated sample cells 141, 142. The sample cells 141, 142 are electrically connected to a common electrode 153 and to respective cell electrodes 151, 152. In the example shown, the sample cells 141, 142 are arranged electrically in series between the common electrode 153 and the respective cell electrodes 151, 152. Each sample cell 141, 142 is further adapted to receive a respective fluid sample, e.g., a whole-blood sample. The test strip 150 has a selected thickness in and out of the plane of FIG. 1. The cell electrodes 151, 152 can be arranged on the same side of the sample cells 141, 142 as the common electrode 153 in the thickness direction. This is sometimes referred to as a "planar" configuration. Alternatively, each cell electrode 151, 152 can be arranged in the thickness direction on the opposite side of the respective sample cell 141, 142 from the common electrode 153. This is sometimes referred to as a "co-facial" configuration.

The herein described system 10 also includes a test meter 100 which is adapted to receive the test strip 150. The test meter 100 has at least one contained circuit 190, and a processor 186. In at least one version, the processor 186 is configured to detect the presence of the respective fluid sample in one of the sample cells 141, 142 of the received test strip 150 using the contained circuit 190. The processor 186 is also configured to detect a first electrical property of the received respective fluid sample using the circuit 190. The processor 186 is further configured to detect a second electrical property of the respective fluid sample in the other of the sample cells of the received analytical test strip using the circuit. For purposes of this discussion, the terms "first electrical property" and "second electrical property" are herein used to differentiate the properties measured for the first and second fluid samples, respectively. In various aspects, only one electrical property can be measured for each fluid sample. In other aspects, more than one electrical property can be measured for each fluid sample. Examples of electrical properties include impedance (AC, or DC resistance), capacitance, conductivity, potential, permittivity, dielectric properties, and inductance.

According to one version, AC impedance is measured as the electrical property. In this version, the circuit 190 includes an AC voltage source 191 controlled by the processor 186 and in which the AC voltage source is connected to the common electrode 153. The respective cell electrodes 151, 152 are connected via a switching unit 194 to a current detector in the circuit 190, including a resistor 192 disposed in series with the AC voltage source 191. The switching unit 194 selectively connects either the cell electrode 151 or the cell electrode 152 to the resistor 192. The voltage across the resistor 192 is directly proportional to the current through the AC voltage source 191 and the connected one of the cell electrodes 151, 152. An amplifier 193 amplifies the voltage across the resistor 192 to provide a voltage signal to the processor 186 that is representative of current through the common electrode 153 and the selected one of the cell electrodes 151, 152. In various embodiments, in place of the switching unit 194, two separate contained circuits 190 could alternatively be provided; that is, one circuit 190 for each of the cell electrodes 151, 152.

In the described exemplary embodiment, the AC voltage source 191 includes a low-pass filter that receives a square wave from the processor 186 and provides a filtered voltage that is closer to a sinusoid as a result of the filtering. Exemplary low-pass filters for this purpose can include fourth-order filters, multiple feedback low pass filters, as well as Sallen and Key low pass filters.

As noted, the test meter 100 can be a portable (e.g., hand-held) test meter for use with a test strip 150 in the determination of at least one analyte in a bodily fluid sample such as a blood sample. Still referring to FIG. 1, an exemplary test meter 100 includes a housing 104 and a strip port connector 106 (hereinafter also synonymously referred to as an "SPC") that is configured to receive the test strip 150, the latter being insertable into a port of the housing 104. The SPC 106 can include spring contacts, such as prongs, which are suitably arranged so that the test strip 150 can be slid into the SPC 106 to electrically connect the electrodes 151, 152, 153 with the circuit 190. The SPC 106 can also or alternatively include pogo pins, solder bumps, pin or other receptacles, jacks, or other devices for selectively and removably making electrical connections.

Still referring to FIG. 1, the herein exemplary test meter 100 includes a user interface including, e.g., a display 181 and one or more user interface buttons 180. The display 181 can be, for example, a liquid crystal display or a bi-stable display configured to show a screen image. The exemplary screen image shown in FIG. 1 provides exemplary indications of glucose concentration ("120") and of date and time ("3/14/15 8:30 am"), as well as a units indication ("mg/dL"). The display 181 can also present error messages or instructions to a user on how to perform a test (analyte determination).

The test meter 100 can also include other electronic components (not shown) for applying test voltages or other electrical signals to the test strip 150, for measuring an electrochemical response (e.g., plurality of test current values), and further for determining an analyte concentration based on the electrochemical response. To simplify the present descriptions, the figures do not depict all such electronic circuitry.

According to the exemplary embodiment, the circuit 190 is electrically connected to the sample cells 141, 142 of the received test strip 150 via the strip port connector 106. The circuit 190 can be configured to selectively apply an excitation voltage signal to the sample cell in order to provide a resultant electrical signal. The excitation voltage signal can have an excitation voltage and an excitation frequency that is greater than a characteristic frequency of the fluid sample.

According to this exemplary embodiment, the processor 186 is disposed within the housing 104 of the meter 100. The processor 186 can be adapted to detect the fluid sample in either of the sample cells 141, 142 and subsequently cause the circuit 190 to apply the excitation voltage signal to detect the first or second electrical property. For the purposes described herein, the processor 186 can include any suitable microcontroller or micro-processor known to those of skill in the art. One exemplary microcontroller is an MSP430F6636 microcontroller that is commercially available from Texas Instruments, Dallas, Tex. USA. The processor 186 can include, e.g., a field-programmable gate array (FPGA) such as an ALTERA CYCLONE FPGA, a digital signal processor (DSP) such as a Texas Instruments TMS320C6747 DSP, or another suitable processing device adapted to carry out various algorithm(s) as described herein. The processor 186 can include signal-generation and signal-measurement functions, e.g., D/A converters, pulse-train generators, or ND converters. For purposes described herein the processor 186 can poll for the presence of fluid samples in the separate sample cells 141, 142, either simultaneously or sequentially.

In various embodiments, the processor 186 is further configured to present an indication of the first electrical property via the user interface. For example, the first electrical property can be indicative of blood glucose. The processor 186 can determine blood glucose (e.g., in mg/dL, mmol/L, or mM) from the first electrical property and display the determined blood glucose value on the display 181. The indication can also be presented, e.g., via a speaker or other audio device using a speech synthesizer. The second electrical property or an indication thereof can additionally or alternatively be displayed or otherwise presented.

According to various embodiments, the processor 186 is further configured to receive a command input via the user interface. The command input can be, e.g., a signal indicating one of the buttons 180 was pressed. In response to the received command input, the processor 186 is programmed to detect the second electrical property and present an indication of the second electrical property via the user interface, e.g., by showing a blood-glucose value determined from the second electrical property on the display 181.

A memory block 118 of the test meter 100 includes one or more storage device(s), e.g., a code memory (such as random-access memory, RAM, or Flash memory) for storing, e.g., program firmware or software; a data memory (e.g., RAM or fast cache); or a disk (such as a hard drive). Computer program instructions to carry out a suitable algorithm(s) are stored in one of those device(s). According to at least one version, the memory block 118 can also or alternatively be incorporated in the processor 186. A Flash or other nonvolatile memory in the memory block 118 can also contain, e.g., graphics to be displayed on the display 181, text messages to be displayed to a user, calibration data, user settings, or algorithm parameters.

Once the test strip 150 is interfaced with the test meter 100, or prior thereto, a fluid sample (e.g., a whole blood sample or a control-solution sample) is introduced into the first sample cell 141 of the test strip 150. The test strip 150 can include enzymatic reagents that selectively and quantitatively transform an analyte in the fluid sample into another predetermined chemical form. For example, the test strip 150 can be an electrochemical-based analytical test strip configured for the determination of glucose in a whole blood sample. Such a test strip 150 can include an enzymatic reagent containing a mediator, such as ferricyanide, and containing an analyte specific enzyme, such as glucose oxidase or glucose dehydrogenase, so that glucose can be physically transformed into an oxidized form. This transformation is discussed below with reference to FIG. 2.

The processor 186 can use information stored in the memory block 118 in determining an analyte, e.g., in determining a blood glucose concentration, based on the electrochemical response of the analytical test strip. For example, the memory block 118 can store correction tables to adjust the determination of the analyte based on a determined impedance of the test strip 150.

Figure 2:
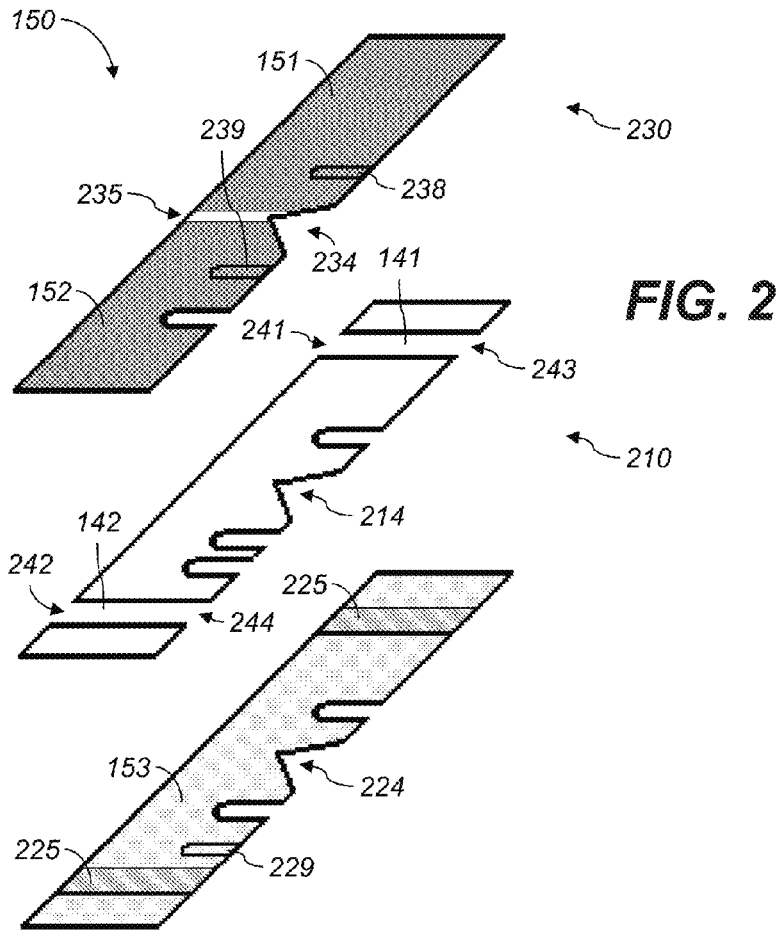
FIG. 2 is an exploded view of an exemplary analytical test strip.

FIG. 2 is an exploded view of an exemplary analytical test strip 150. Additional details of various exemplary test strips and measurement methods are provided in US Patent Application Publication No. 2007/0074977, incorporated herein by reference in its entirety. According to the exemplary embodiment depicted, the test strip 150 is an electrochemical-based analytical test strip that is configured for the determination of glucose in an applied whole blood sample. According to this version, the test strip 150 includes two sample cells 141, 142. Each of the sample cells 141, 142 includes a respective reagent 255, as discussed below. The respective reagents 225 can have the same chemistry as each other, or can have different chemistries.

The exemplary test strip 150 includes a patterned definition layer 210 defining two fluidically separated sample cells 141, 142. The patterned definition layer 210 can also be referred to as a "spacer layer." The patterned definition layer 210 can be electrically insulating. In this example, the patterned definition layer 210 includes multiple separate segments. Alternatively, however, the patterned definition layer 210 can also include only one connected segment. The definition layer can be substantially planar as depicted herein, or can include one or more segments that curve out of a plane.

Each sample cell 141, 142 has a respective port 241, 242 on a perimeter of the test strip 150. In this example, each sample cell 141, 142 has two ports 241, 243, 242, 244, as shown. Test strip 150 can alternatively or additionally include a vent (not shown), or one of the ports 241, 243, 242, 244 can operate as a vent. Each sample cell 141, 142 is further adapted to receive a respective fluid sample via one of the respective ports 241, 243, 242, 244.

The ports 241, 242 are arranged so that respective fluid samples can be drawn into the respective sample cells 141, 142 under capillary action. This capillary action can occur as a fluid sample is brought into contact with edges or sidewalls of either of the ports 241, 242. In the example shown, the sample cell 141 has laterally-opposed ports 241, 243. The sample cell 142 has two laterally-opposed ports 242, 244. The ports 241, 242 are disposed along one edge of the test strip 150 and the opposed ports 243, 244 are disposed along an opposite edge of the test strip 150. One of the ports 241, 243, 242, 244 of each sample cell 141, 142 can provide a sample inlet and the other port can act as a vent to permit air to escape as the air is displaced by fluid entering the corresponding sample cell 141, 142.

In various aspects, the sample cells 141, 142 are adapted for analyzing small-volume samples. For example, each sample cell 141, 142 can have a volume ranging from about 0.1 microliters to about 5 microliters, a volume ranging from about 0.2 microliters to about 3 microliters, or a volume ranging from about 0.3 microliters to about 1 microliter. To accommodate a small sample volume, the electrodes 151 and 153, and the electrodes 152 and 153, can be closely spaced in relation to one another. The height of the patterned definition layer 210, as shown, defines the distance between, e.g., the cell electrode 151 and the common electrode 153. To provide sample cell volumes in the above ranges, the height of the patterned definition layer 210 can be in the range of about 1 micron to about 500 microns, or in the range of between about 10 microns and about 400 microns, or in the range of between about 40 microns and about 200 microns. Further details relating to the construction, design and features of exemplary test strips are given in U.S. Pat. No. 8,163,162, incorporated herein by reference in its entirety.

According to this exemplary embodiment, a reagent 225 can be disposed within either sample cell 141, 142 using a process such as slot-die coating, flexo printing, gravure printing, coating such as by dispensing liquid from the end of a tube, ink jetting, or screen printing. Such processes are described, for example, in U.S. Pat. Nos. 6,676,995; 6,689,411; 6,749,887; 6,830,934; and 7,291,256; in U.S. Patent Application Publication No. 2004/0120848; and in PCT Application Publication No. WO/1997/018465 and U.S. Pat. No. 6,444,115, each of which is incorporated herein in relevant part by reference. The reagent 225 can include a mediator and an enzyme, and be deposited onto or affixed to the common electrode 153 or the corresponding one of the cell electrodes 151, 152. Suitable mediators include ferricyanide, ferrocene, ferrocene derivatives, osmium pipyridyl complexes, quinone derivatives, and ruthenium derivatives. Suitable enzymes include glucose oxidase, glucose dehydrogenase (GDH) based on pyrroloquinoline quinone (PQQ) co-factor, GDH based on nicotinamide adenine dinucleotide (NAD) co-factor, and GDH based on a flavin adenine dinucleotide (FAD) co-factor (EC 1.1.99.10). Exemplary reagents useful with various aspects are described in U.S. Pat. No. 7,291,256, incorporated herein by reference. The reagent 225 can also include a buffer, a wetting agent, or a stabilizer for a biochemical component.

The common electrode 153 is arranged over the patterned definition layer 210 and in electrical communication with each of the sample cells 141, 142. In various aspects, the reagent 225 is arranged over the common electrode 153 so as to be positioned within the respective sample cell 141, 142 of the assembled test strip 150. Two cell electrodes 151, 152 are also arranged so that each electrode 151, 152 is in electrical communication with a respective one of the sample cells 141, 142.

In this example, the cell electrodes 151, 152 are substantially parallel to the common electrode 153 and electrically isolated therefrom. Accordingly, two capacitors are defined, a first capacitor between the cell electrode 151 and the common electrode 153, and a second capacitor between the cell electrode 152 and the common electrode 153. In various embodiments, the electrodes 151, 152, 153 can be arranged spaced apart in a facing or opposing faced arrangement, or alternatively in other coplanar or non-coplanar configurations.

A top insulator (not shown) can be disposed over the cell electrodes 151, 152 so as to fully or partially cover each. Similarly, a bottom insulator (not shown) can be disposed beneath the common electrode 153 and disposed to either cover the whole surface or a portion thereof. A support (not shown), e.g., MYLAR or polyester, can be included to provide mechanical support to the test strip. The terms "top" and "bottom" are not limiting with respect to orientation or relative placement, but merely serve to distinguish the top insulator from the bottom insulator. For example, either the top insulator or the bottom insulator can be selected to be closer to the user when the test strip 150 is inserted into the test meter 100.

For purposes of the exemplary embodiment, the electrodes 151, 152, 153 can be thin films. In various aspects, the electrodes can include conductive material formed from materials such as gold, palladium, carbon, allotropes of carbon, silver, platinum, tin oxide, iridium, indium, and combinations thereof (e.g., indium-doped tin oxide or "ITO"). The electrodes can be formed by disposing a conductive material onto the top and bottom insulators by a sputtering, electroless plating, thermal evaporation, or solids-deposition methods such as screen printing, flexo printing, slot-dye coating, or other processes. In an example, the common electrode 153 is a sputtered gold electrode disposed over the bottom insulator and the cell electrodes 151, 152 are formed from a sputtered palladium layer disposed over the top insulator. Suitable materials that can be employed in the top and bottom insulators include, for example, plastics (e.g. PET, PETG, polyimide, polycarbonate, polystyrene), silicon, ceramic, glass, and combinations thereof. For example, the top and bottom insulators can be formed from 7 mil polyester substrate(s).

The patterned definition layer 210, the common electrode 153, and each respective cell electrode 151, 152 are arranged to expose a surface portion 229 of the common electrode and respective surface portions 238, 239 of the cell electrodes 151, 152. The surface portions 229, 238, 239 can be substantially planar. These surface portions 229, 238, and 239 can be contacted by electrodes in the SPC 106, FIG. 1, when the test strip is engaged with the test meter wherein the circuit 190, FIG. 1, can electrically communicate with the common electrode 153 and the cell electrodes 151, 152 in order to determine electrical properties of fluid samples in the sample cells 141, 142. An example is discussed below with reference to FIG. 3.

Still referring to FIG. 2, the cell electrodes 151, 152 are defined by a substantially planar cell-electrode layer 230 in this example. According to this embodiment, this layer 230 includes a support, e.g., of plastic, having a coating of a conductive material, e.g., palladium (Pd) or gold (Au). The layer 230 has an electrical discontinuity 235 separating the cell electrodes 151, 152 from each other. The electrical discontinuity can be formed by patterning the conductive material, e.g., by sputtering, or by scoring, laser ablating, or otherwise removing conductive material from the layer 230 after fabrication. In other embodiments, the cell electrodes 151, 152, or the common electrode 153, include discrete wire or other electrically-conductive structures. In the herein described version, the common electrode 153 has, a 15 nm Au layer sputtered on a transparent polyester film. The cell electrodes 151, 152 each include a 15 nm Pd layer sputtered on polyester film. The patterned definition layer 210 includes a 95 μm white polyester layer. These specific thicknesses, as noted, are exemplary and can be suitably altered.

In various embodiments, the patterned definition layer 210 is patterned to define an alignment feature 214. In this example, the common electrode 153 and the layer 230 are also similarly patterned to define respective alignment features 224, 234 that correspond to the alignment feature 214. In this specific example, the alignment features 214, 224, 234 are notches, but at least one of the alignment features 214, 224, 234 could alternatively include protrusions. Moreover, the alignment features 214, 224, 234 can be the same shape or different shapes.

Figure 3:
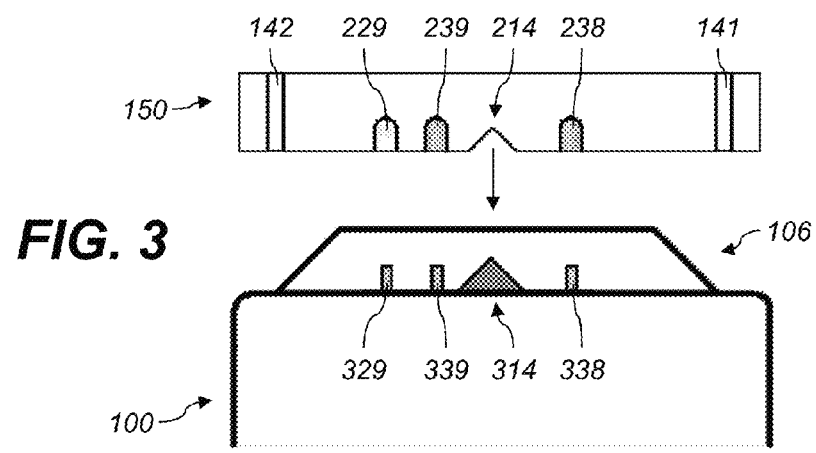
FIG. 3 shows an exemplary test strip and an exemplary test meter adapted to receive the exemplary test strip.

FIG. 3 shows the test strip 150 and the test meter 100 for purposes of engagement. As previously discussed, the test strip 150 is defined by the fluidically separate sample cells 141, 142, an alignment feature 214, and spaced portions 229, 238, and 239, as discussed above with reference to FIG. 2. The test meter 100 includes the SPC 106 that is configured to receive the test strip 150.

The SPC 106 includes a protrusion 314 adapted to mate with the alignment feature 214 when the test strip 150 is properly inserted in the SPC 106. More specifically, the protrusion 314 prevents the test strip 150 from being inserted with the alignment feature 214 oriented away from the test meter 100. In various aspects, the test strip 150 and the test meter 100 can include respective alignment features (not shown) that are configured to block electrical contact between the circuit 190, FIG. 1, and one or more of the electrodes 153, 151, 152 unless the test strip 150 is properly inserted.

The SPC 106 further includes a set of spaced contacts 329, 338, 338 having a spacing therebetween that corresponds with the spacings defined between each of the surface portions 229, 238 and 239 to enable electrical connection to the circuit 190, FIG. 1. When the test strip 150 is correctly inserted in the SPC 106, the contacts 329, 338, 339 make electrical connections with the surface portions 229, 238, and 239, and thus with the electrodes 153, 151, 152, respectively of the properly inserted test strip 150.

In an example, the test strip 150 has a width dimension of approximately 30±5 mm and a length dimension (shown vertically in the depicted version of FIG. 3) of approximately 7±5 mm. According to this specific embodiment, the alignment feature 214 can be centered in the test strip 150 along the horizontal direction, as shown. The surface portion 238 can be centered 5±2 mm horizontally away from the center of the alignment feature 214. However, it will be readily apparent that the dimensions of the test strip can be selected, for example, to permit effective handling by users. Moreover, the dimensions of the sample cells 141, 142 can be selected to provide a desired measurement time or measurement accuracy.

In various embodiments, the SPC 106 includes a supplemental contact (not shown) electrically isolated from a selected one of the contacts 329, 338, 339 and adapted to make electrical contact with the surface portion 229, 238, 239 corresponding to the selected contact. The test meter 100, FIG. 1, can measure the resistance or electrical continuity between the selected contact and the supplemental contact. When the test strip 150 is properly inserted into the test meter 100, the corresponding portion shorts the selected contact to the supplemental contact and the resistance decreases sharply. According to at least one version, this decrease in resistance can wake up the processor 186 from a low-power (passive or sleep) mode and initiate a fluid-detection cycle. Once a determination is made that the test strip 150 is electrically connected to the test meter 100, the test meter 100 can apply a test potential or current, e.g., a constant current, across one or both of the sample chambers 141, 142. In an example, a constant DC current can be applied to one of the sample cells 141, 142, wherein the voltage across that sample cell 141, 142 can be monitored. When the fluid sample has filled the initially selected sample cell 141, 142, the voltage across that sample cell 141, 142 will fall below a selected threshold. AC signals, as described herein, can be measured before the selected sample cell 141, 142 has filled with fluid, or alternatively after filling.

Figure 4:
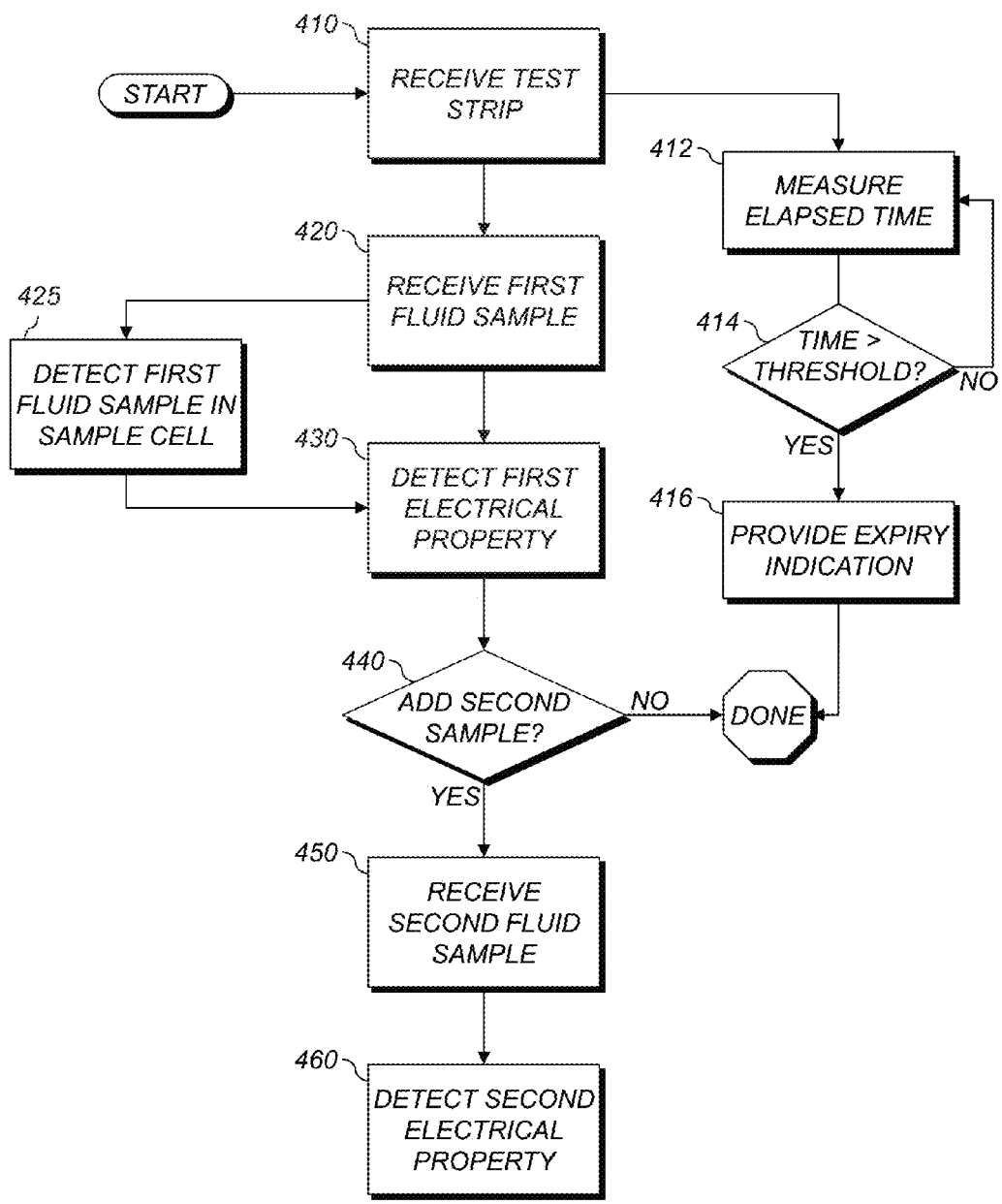
FIG. 4 is a flow diagram depicting stages in exemplary methods for testing a fluid sample using an analytical test strip.

FIG. 4 is a flow diagram depicting stages in an exemplary method for testing a fluid sample using an analytical test strip as herein described. Reference is made to various components described above for exemplary purposes. Methods described herein are not limited to being performed only by the identified components.

According to this exemplary method 400, at step 410, an analytical test strip 150, FIG. 1, having a first sample cell 141 and a fluidically-separate second sample cell 142, both FIG. 1, is initially provided or received.

At step 420, a first fluid sample is received through introduction to one of the sample cells (e.g., sample cell 141) of the received test strip 150. The determination of which sample cell on the test strip 150 is "first" for purposes of this step of the method can be determined by which sample cell receives fluid sample initially. In other versions, this latter determination can also be made based upon the construction of the test strip 150. For example, if a specific sample cell is the "first" sample cell, markings or other indicia on the test strip 150 or the test meter 100, FIG. 1, can be provided to indicate to a user which sample cell is the first sample cell 141.

At step 430, a first electrical property of the first fluid sample is detected.

At decision step 440, it is determined whether a second fluid sample should be added to the other sample cell (the second sample cell 142) on the test strip 150. If not, the method can terminate. If so, the next step can be step 450.

At step 450, a determination is made that the second fluid sample should be added. Accordingly, the second fluid sample is received by the test strip in which the second fluid sample is introduced to the second sample cell of the received analytical test strip.

At step 460, a second electrical property of the second fluid sample is detected. As discussed above, "second" is used for clarity of identification. It is not required to determine two separate electrical properties of the second fluid sample or to repeat the determination of one electrical property twice for the second fluid sample (although both are done, individually or together, in various embodiments).

In various aspects, at least one of the steps described herein is carried out by the processor 186 in the test meter 100, both FIG. 1. Specifically, the receiving-test-strip step 410 can include receiving the analytical test strip 150 in the test meter 100. The detecting step 430 can then include automatically detecting the first and second electrical properties using the processor 186 of the test meter 100.

In various aspects, the test meter 100 includes a common terminal (i.e., the contact 329, FIG. 3) and first and second sample-cell terminals (i.e., the contacts 338, 339, FIG. 3). The common terminal (contact 329) is electrically connected to both the first and the second sample cells 141, 142 in the received test strip 150. The first and second sample-cell terminals (the contacts 338, 339) are electrically connected to the first and second sample cells 141, 142 in the received test strip 150, respectively. The processor 186 is operatively connected to the common terminal (the contact 329) and the first and second sample-cell terminals (the contacts 338, 339) to determine the first and second electrical properties.

At step 425, the presence of the first fluid sample in the first sample cell of the received analytical test strip can be automatically detected using the processor 186. This detection can be done in various ways.

For example and according to one embodiment, the processor 186 automatically polls the first and second sample cells 141, 142 in order to detect the presence of the first fluid sample.

In at least one version, the processor 186 performs the polling of the sample cells by operating the contained circuit 190 to apply polling electrical signals to a first current path through the first sample-cell terminal (the contact 338, FIG. 3) and the common terminal (the contact 329, FIG. 3). Polling electrical signals are likewise separately applied to a second current path through the second sample-cell terminal (the contact 339, FIG. 3) and the common terminal (the contact 329). The processor 186, using the circuit 190, measures respective response electrical signals, and automatically detects the presence of the first fluid sample in the first sample cell 141 of the received test strip 150 from the respective response electrical signals using the processor 186.

Various embodiments use test strips 150 that have a limited useful life. For example, blood-glucose test strips are often stored in a vial or other specialized container. After removal from the vial, the strip is useful to measure blood glucose for a certain amount of time. After that time, the strip should be discarded, since its accuracy decreases over time out of the vial. An exemplary limit for out-of-vial time of a blood-glucose test strip is two minutes. In these embodiments, steps 412, 414, and 416 can be performed in parallel with, or interleaved between, other steps shown in FIG. 4.

At step 412, a time elapsed since the analytical test strip was received is measured. For example, the processor 186, FIG. 1, can start a timer when it detects insertion of the test strip 150 into the SPC 106.

At decision step 414, it is determined whether the elapsed time exceeds a selected threshold. If not, the next step is step 412 (or another step described herein); that is, normal operation continues. If the elapsed time does exceed the threshold, the next step is step 416.

At step 416, an expiry indication via a user interface. For example, a message can be displayed on the display 181, FIG. 1, or an audible indication can be provided via a speaker or a headphone jack in the test meter 100. The processor 186 can alternatively indicate expiry of the timer by deactivating the test meter 100. This can reduce the probability of unintentionally using an expired test strip, and can extend the battery life of a battery-operated test meter 100.

Figure 5:
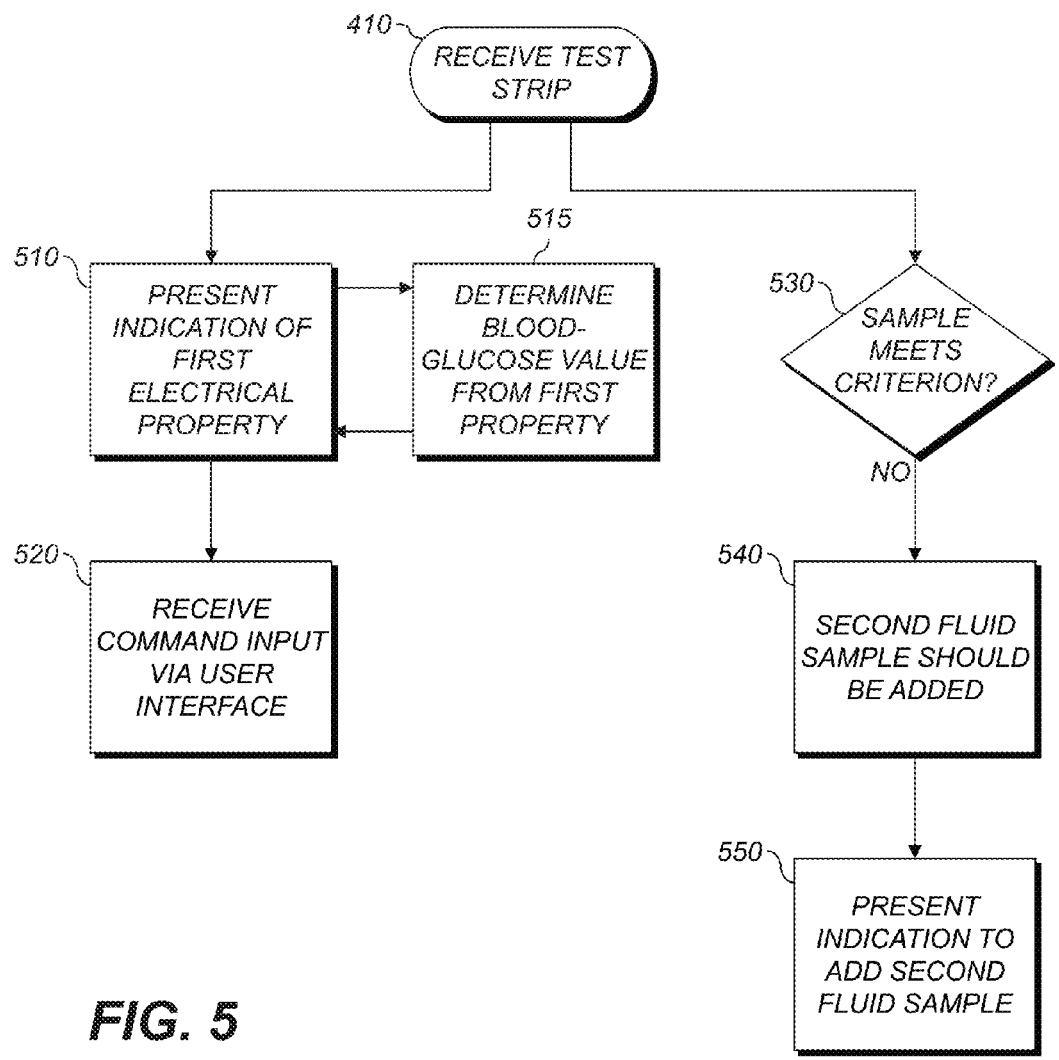
FIG. 5 is a flow diagram depicting stages for determining whether a second sample should be added to a test strip according to various embodiments.

FIG. 5 is a flow diagram depicting stages in the decision step 440, FIG. 4, according to various embodiments. In some embodiments, the decision step 440 includes steps 510, 515, and 520. In other embodiments, the decision step 440 includes steps 530, 540, and 550. Each of these steps are herein described in greater detail.

At step 510, an indication of the first electrical property is presented via a user interface of the test meter 100. Step 510 can include step 515.

At step 515, a blood-glucose value is determined from the first electrical property, e.g., by the processor 186. In some embodiments using step 515, step 510 also includes presenting the determined blood-glucose value, e.g., on the display 181 or via an audio output.

At step 520 and after step 510, a command input is received via the user interface. The decision step 440 then includes making a determination as to whether the second fluid sample should be added in response to the received command input. As discussed above, the command input can be, e.g., a signal indicating one of the buttons 180 was pressed. In response to that command input, a determination can be made that the second fluid sample should be added. Step 520 can be performed even if step 510 is not performed. For example, the user can be provided with a user-interface option to perform a retest using the second sample cell 142 at the user's discretion, regardless of whether information has been presented.

In various embodiments and at decision step 530, a determination is made as to whether the first fluid sample meets a selected criterion. This determination can be made automatically using the processor 186. If not, the next step is step 540. At step 540, it is determined that that the second fluid sample should be added, since the first fluid sample fails to meet the selected criterion. These embodiments advantageously provide automatic detection of various conditions that may lead to reduced accuracy of measurement results. The user then has an opportunity to perform a re-test using the same test strip, without (e.g.) taking the time to remove the first test strip from the test meter, retrieve another test strip from a supply vial, and insert the new test strip in the test meter. This feature can be particularly beneficial for users with reduced manual dexterity such as some elderly or arthritic diabetics.

In various embodiments, the selected criterion is a proportion of the volume of the first sample cell 141 to be filled by the first fluid sample. This proportion can be expressed as a percentage of volume or as an absolute volume, provided the volume of the first sample cell 141 is known. In some embodiments, the detecting step 430 includes detecting a capacitance of the first sample cell 141. The dielectric constants of most fluids are higher than the dielectric constant of air under similar environmental conditions, so capacitance can increase as the sample cell 141 fills. Capacitance measurements can therefore be used to determine the volume of fluid in the first sample cell 141.

Various techniques for determining whether the volume of fluid is sufficient for a measurement are described in U.S. Pat. No. 6,193,873 and U.S. Pat. No. 7,199,594, each of which is incorporated herein by reference. The processor 186 can carry out measurements and analyses described in these patents, and prompt the user to provide a second fluid sample if the volume is inadequate. For example, as described in U.S. Pat. No. 6,193,873, the processor 186 can operate the contained circuit 190 to apply a constant current across one or both of the sample cells 141, 142, either simultaneously or sequentially, e.g., using a constant-current supply (not shown). The circuit 190 can include a voltmeter (not shown) for measuring the voltage across the sample cell 141, i.e., between the cell electrode 151 and the common electrode 153, or across the sample cell 142, i.e., between the cell electrode 152 and the common electrode 153. When the voltage on either of the sample cells 141, 142 falls below a selected threshold, the processor 186 can determine that a sample is present in that one of the sample cells 141, 142. The voltage can fall below the threshold, e.g., because the fluid has come into contact with both of the electrodes 151, 153 or 152, 153. In another example, as described in U.S. Pat. No. 7,199,594, the processor 186 can operate the circuit 190 to apply AC voltage across one or both of the sample cells 141, 142, e.g., using the AC voltage source 191. The current through the sample cell(s) 141, 142 can be measured and capacitance determined from the measured current, e.g., by synchronously demodulating and low-pass filtering the current.

At step 550, the prompting for insertion of a second fluid sample is carried out. Specifically, the processor 186 presents, via the user interface (e.g., the display 181), an indication that the second fluid sample should be added to the test strip. The processor 186 can then poll or wait until the second fluid sample has been added, then step 460 can be carried out.

Using methods, devices or systems described herein, successive measurements can be taken rapidly. This can advantageously permit more accurately determining analytes in fluid samples. Various embodiments increase user convenience and user control over retesting.

PARTS LIST FOR FIGS. 1-5

10 system
100 test meter
104 housing
106 strip port connector
118 memory block
141, 142 sample cells
150 analytical test strip
151, 152 cell electrodes
153 common electrode
180 button
181 display
186 processor
190 contained circuit
191 AC voltage source
192 resistor
193 amplifier
194 switching unit
210 patterned definition layer
214, 224 alignment features
225 reagent
229 surface portion
230 cell-electrode layer
234 alignment feature
235 electrical discontinuity
238, 239 surface portions 241, 242, 243, 244 ports
314 protrusion
329, 338, 339 contacts
400 method
410, 412 steps
414 decision step
416, 420, 430 steps
440 decision step
450, 460 steps
510, 515, 520 steps
530 decision step
540, 550 steps While preferred embodiments of the present invention have been shown and described herein, it will be obvious to those skilled in the art that such embodiments are provided in this description by way of example only. To that end, numerous variations, changes, and substitutions will be readily apparent to those skilled in the art without departing from the invention. For example, the user of a test meter can be prompted, e.g., via a display on the test meter, to apply fluid samples, e.g., blood samples, to both sample cells in quick succession. Each fluid sample can be measured once it has filled the corresponding cell. This can reduce the effect of electrical noise by providing two data points that are substantially the same biologically (e.g., two drops of blood from a single fingerstick).

In addition, it should be understood that various alternatives to the embodiments of the invention described herein can be employed in practicing the invention. References to "a particular embodiment" (or "aspect") and the like refer to features that are present in at least one embodiment of the invention. Separate references to "an embodiment" or "particular embodiments" or the like, however, do not necessarily refer to the same embodiment or embodiments; however, such embodiments are not mutually exclusive, unless specifically indicated or as are readily apparent to one of skill in the art. The word "or" is used in this disclosure in a non-exclusive sense, unless otherwise explicitly noted. It is intended that the following claims define the scope of the invention and that devices and methods within the scope of these claims and their equivalents be covered thereby.

What is claimed is:

1. An analytical test strip, comprising:
a patterned definition layer defining two fluidically separated sample cells, each sample cell having a port on a perimeter of the analytical test strip and being adapted to receive a respective fluid sample via the respective port;
a common electrode arranged over the definition layer and in electrical communication with each of the sample cells; and
two cell electrodes, each electrode in electrical communication with a respective one of the sample cells;
wherein the definition layer, the common electrode, and the cell electrodes are arranged to expose a surface portion of the common electrode and respective surface portions of the cell electrodes.

2. The test strip according to claim 1, wherein the cell electrodes are defined by a substantially planar cell-electrode layer having an electrical discontinuity separating the cell electrodes.

3. The test strip according to claim 2, wherein the cell-electrode layer includes gold.

4. The test strip according to claim 1, wherein the definition layer is patterned to define an alignment feature.

5. The test strip according to claim 1, wherein the definition layer is substantially planar.

6. The test strip according to claim 1, wherein the test strip is an electrochemical-based analytical test strip configured for a determination of glucose in a whole blood sample and including a respective reagent in each of the sample cells.

7. A method for testing a fluid sample using an analytical test strip, the method comprising:
receiving the analytical test strip having a first sample cell and a fluidically-separate second sample cell;
receiving a first fluid sample introduced to the first sample cell of the received analytical test strip;
detecting a first electrical property of the first fluid sample; and
determining whether a second fluid sample should be added to the second sample cell.

8. The method according to claim 7, further including, if the second fluid sample should be added:
receiving the second fluid sample introduced to the second sample cell of the received analytical test strip; and
detecting a second electrical property of the second fluid sample.

9. The method according to claim 8, wherein the receiving-test-strip step includes receiving the analytical test strip in a test meter and the detecting step includes automatically detecting the first and second electrical properties using a processor of the test meter.

10. The method according to claim 9, further including automatically detecting a presence of the first fluid sample in the first sample cell of the received analytical test strip using the processor.

11. The method according to claim 9, further including automatically polling the first and second sample cells using the processor to detect the presence of the first fluid sample.

12. The method according to claim 9, further including presenting an indication of the first electrical property via a user interface of the test meter and subsequently receiving a command input via the user interface, wherein the determining step includes determining that the second fluid sample should be added in response to the received command input.

13. The method according to claim 12, further including determining a blood-glucose value from the first electrical property, wherein the presenting step includes presenting the determined blood-glucose value.

14. The method according to claim 9, wherein the test meter includes a common terminal and first and second sample-cell terminals, the common terminal is electrically connected to both the first and the second sample cells in the received analytical test strip, and the first and second sample-cell terminals are electrically connected to the first and second sample cells in the received analytical test strip, respectively, wherein the processor is operatively connected to the common terminal and the first and second sample-cell terminals to determine the first and second electrical properties.

15. The method according to claim 7, further including automatically determining whether the first fluid sample meets a selected criterion using a processor and determining that the second fluid sample should be added if the first fluid sample does not meet the selected criterion.

16. The method according to claim 15, wherein the selected criterion is a proportion of a volume of the first sample cell to be filled by the first fluid sample and the detecting step includes detecting a capacitance of the first sample cell.

17. The method according to claim 7, further including measuring a time elapsed since the analytical test strip was received, and providing an expiry indication via a user interface when the elapsed time exceeds a selected threshold.

18. An analyte measurement system comprising:
- an analytical test strip comprising a patterned layer defining two fluidically separated sample cells electrically connected to a common electrode and to respective cell electrodes, each sample cell being adapted to receive a respective fluid sample; and
- a test meter adapted to receive the analytical test strip, the test meter having a contained circuit and a processor, the processor being configured to detect the presence of the respective fluid sample in one of the sample cells of the received analytical test strip and detect a first electrical property of the received respective fluid sample using the contained circuit,
- wherein the processor is configured to detect a second electrical property of the respective fluid sample in the other of the sample cells of the received analytical test strip using the circuit.

19. The system according to claim 18, the test meter further including a user interface and the processor further configured to present an indication of the first electrical property via the user interface.

20. The system according to claim 18, the test meter further including a user interface and the processor further configured to receive a command input via the user interface and, in response to the received command input, detect the second electrical property and present an indication of the second electrical property via the user interface.

* * * * *